US010413298B2

(12) United States Patent
Williams

(10) Patent No.: US 10,413,298 B2
(45) Date of Patent: Sep. 17, 2019

(54) ADAPTER ASSEMBLY FOR SURGICAL DEVICES

(71) Applicant: Covidien LP, Mansfield, MA (US)

(72) Inventor: Justin Williams, Southbury, CT (US)

(73) Assignee: Covidien LP, Mansfield, MA (US)

(*) Notice: Subject to any disclaimer, the term of this patent is extended or adjusted under 35 U.S.C. 154(b) by 803 days.

(21) Appl. No.: 14/882,550

(22) Filed: Oct. 14, 2015

(65) Prior Publication Data

US 2017/0105735 A1 Apr. 20, 2017

(51) Int. Cl.

| | |
|---|---|
| ***A61B 17/115*** | (2006.01) |
| ***A61B 17/34*** | (2006.01) |
| ***A61B 17/00*** | (2006.01) |

(52) U.S. Cl.

CPC .......... *A61B 17/1155* (2013.01); *A61B 17/34* (2013.01); *A61B 2017/0046* (2013.01); *A61B 2017/00367* (2013.01); *A61B 2017/00398* (2013.01); *A61B 2017/00477* (2013.01)

(58) Field of Classification Search

CPC ... A61B 17/068; A61B 17/1155; A61B 17/34; A61B 2017/1157; A61B 2017/00398; A61B 2017/0046; A61B 2017/00477; B25B 17/00; B25B 17/02; B25B 21/00

USPC ........ 606/1, 41, 130, 170; 227/178.1, 176.1, 227/180.1, 175.1, 175.2, 181.1, 182.1, 227/177.1; 81/57.31, 57.3

See application file for complete search history.

(56) References Cited

U.S. PATENT DOCUMENTS

| | | | |
|---|---|---|---|
| 2,777,340 | A | 1/1957 | Hettwer et al. |
| 2,957,353 | A | 10/1960 | Babacz |
| 3,111,328 | A | 11/1963 | Di Rito et al. |
| 3,695,058 | A | 10/1972 | Keith, Jr. |
| 3,734,515 | A | 5/1973 | Dudek |
| 3,759,336 | A | 9/1973 | Marcovitz et al. |
| 4,162,399 | A | 7/1979 | Hudson |
| 4,606,343 | A | 8/1986 | Conta et al. |
| 4,705,038 | A | 11/1987 | Sjostrom et al. |
| 4,722,685 | A | 2/1988 | de Estrada et al. |
| 4,823,807 | A | 4/1989 | Russell et al. |
| 4,874,181 | A | 10/1989 | Hsu |
| 5,129,118 | A | 7/1992 | Walmesley |
| 5,129,570 | A | 7/1992 | Schulze et al. |
| 5,152,744 | A | 10/1992 | Krause et al. |

(Continued)

FOREIGN PATENT DOCUMENTS

| | | |
|---|---|---|
| CA | 2451558 A1 | 1/2003 |
| CA | 2824590 A1 | 4/2014 |

(Continued)

OTHER PUBLICATIONS

Extended European Search Report corresponding to International Application No. EP 15 15 1076.5 dated Apr. 22, 2015.

(Continued)

*Primary Examiner* — David B. Thomas

(57) ABSTRACT

An adapter assembly for connecting an end effector to a handle assembly includes first, second, and third drive assemblies configured for converting rotational motion from the handle assembly to linear motion for performing first, second, and third functions. Each of the first, second, and third drive assemblies defining a longitudinal axes, wherein at least two of the longitudinal axes of the first, second, and third drive assemblies are co-axial.

17 Claims, 10 Drawing Sheets

(56) References Cited

U.S. PATENT DOCUMENTS 5,301,061 A 4/1994 Nakada et al.
5,312,023 A 5/1994 Green et al.
5,326,013 A 7/1994 Green et al.
5,350,355 A 9/1994 Sklar
5,383,874 A 1/1995 Jackson et al.
5,383,880 A 1/1995 Hooven
5,389,098 A 2/1995 Tsuruta et al.
5,395,033 A 3/1995 Byrne et al.
5,400,267 A 3/1995 Denen et al.
5,411,508 A 5/1995 Bessler et al.
5,413,267 A 5/1995 Solyntjes et al.
5,427,087 A 6/1995 Ito et al.
5,433,721 A * 7/1995 Hooven .............. A61B 17/068
227/175.1
5,467,911 A 11/1995 Tsuruta et al.
5,476,379 A 12/1995 Disel
5,487,499 A 1/1996 Sorrentino et al.
5,518,163 A 5/1996 Hooven
5,518,164 A 5/1996 Hooven
5,526,822 A 6/1996 Burbank et al.
5,529,235 A 6/1996 Boiarski et al.
5,535,934 A 7/1996 Boiarski et al.
5,535,937 A 7/1996 Boiarski et al.
5,540,375 A 7/1996 Bolanos et al.
5,540,706 A 7/1996 Aust et al.
5,542,594 A 8/1996 McKean et al.
5,549,637 A 8/1996 Crainich
5,553,675 A 9/1996 Pitzen et al.
5,562,239 A 10/1996 Boiarski et al.
5,564,615 A 10/1996 Bishop et al.
5,609,560 A 3/1997 Ichikawa et al.
5,626,587 A 5/1997 Bishop et al.
5,632,432 A 5/1997 Schulze et al.
5,645,209 A 7/1997 Green et al.
5,647,526 A 7/1997 Green et al.
5,653,374 A 8/1997 Young et al.
5,658,300 A 8/1997 Bito et al.
5,662,662 A 9/1997 Bishop et al.
5,667,517 A 9/1997 Hooven
5,693,042 A 12/1997 Boiarski et al.
5,704,534 A 1/1998 Huitema et al.
5,713,505 A 2/1998 Huitema
5,762,603 A 6/1998 Thompson
5,779,130 A 7/1998 Alesi et al.
5,782,396 A 7/1998 Mastri et al.
5,782,397 A 7/1998 Koukline
5,792,573 A 8/1998 Pitzen et al.
5,797,536 A 8/1998 Smith et al.
5,820,009 A 10/1998 Melling et al.
5,863,159 A 1/1999 Lasko
5,908,427 A 6/1999 McKean et al.
5,954,259 A 9/1999 Viola et al.
5,964,774 A 10/1999 McKean et al.
5,993,454 A 11/1999 Longo
6,010,054 A 1/2000 Johnson et al.
6,017,354 A 1/2000 Culp et al.
6,032,849 A 3/2000 Mastri et al.
6,045,560 A 4/2000 McKean et al.
6,090,123 A 7/2000 Culp et al.
6,126,651 A 10/2000 Mayer
6,129,547 A 10/2000 Cise et al.
6,165,169 A 12/2000 Panescu et al.
6,239,732 B1 5/2001 Cusey
6,241,139 B1 6/2001 Milliman et al.
6,264,086 B1 7/2001 McGuckin, Jr.
6,264,087 B1 7/2001 Whitman
6,302,311 B1 10/2001 Adams et al.
6,315,184 B1 11/2001 Whitman
6,321,855 B1 11/2001 Barnes
6,329,778 B1 12/2001 Culp et al.
6,343,731 B1 2/2002 Adams et al.
6,348,061 B1 2/2002 Whitman
6,368,324 B1 4/2002 Dinger et al.
6,371,909 B1 4/2002 Hoeg et al.
6,434,507 B1 8/2002 Clayton et al.
6,443,973 B1 9/2002 Whitman
6,461,372 B1 10/2002 Jensen et al.
6,488,197 B1 12/2002 Whitman
6,491,201 B1 12/2002 Whitman
6,533,157 B1 3/2003 Whitman
6,537,280 B2 3/2003 Dinger et al.
6,610,066 B2 8/2003 Dinger et al.
6,611,793 B1 8/2003 Burnside et al.
6,645,218 B1 11/2003 Cassidy et al.
6,654,999 B2 12/2003 Stoddard et al.
6,698,643 B2 3/2004 Whitman
6,699,177 B1 3/2004 Wang et al.
6,716,233 B1 4/2004 Whitman
6,743,240 B2 6/2004 Smith et al.
6,783,533 B2 8/2004 Green et al.
6,792,390 B1 9/2004 Burnside et al.
6,793,652 B1 9/2004 Whitman et al.
6,817,508 B1 11/2004 Racenet et al.
6,830,174 B2 12/2004 Hillstead et al.
6,846,308 B2 1/2005 Whitman et al.
6,846,309 B2 1/2005 Whitman et al.
6,849,071 B2 2/2005 Whitman et al.
6,860,892 B1 3/2005 Tanaka et al.
6,899,538 B2 5/2005 Matoba
6,905,057 B2 6/2005 Swayze et al.
6,959,852 B2 11/2005 Shelton, IV et al.
6,964,363 B2 11/2005 Wales et al.
6,981,628 B2 1/2006 Wales
6,981,941 B2 1/2006 Whitman et al.
6,986,451 B1 1/2006 Mastri et al.
6,988,649 B2 1/2006 Shelton, IV et al.
7,032,798 B2 4/2006 Whitman et al.
RE39,152 E 6/2006 Aust et al.
7,055,731 B2 6/2006 Shelton, IV et al.
7,059,508 B2 6/2006 Shelton, IV et al.
7,077,856 B2 7/2006 Whitman
7,111,769 B2 9/2006 Wales et al.
7,122,029 B2 10/2006 Koop et al.
7,140,528 B2 11/2006 Shelton, IV
7,141,049 B2 11/2006 Stern et al.
7,143,923 B2 12/2006 Shelton, IV et al.
7,143,925 B2 12/2006 Shelton, IV et al.
7,143,926 B2 12/2006 Shelton, IV et al.
7,147,138 B2 12/2006 Shelton, IV
7,172,104 B2 2/2007 Scirica et al.
7,225,964 B2 6/2007 Mastri et al.
7,238,021 B1 7/2007 Johnson
7,246,734 B2 7/2007 Shelton, IV
7,252,660 B2 8/2007 Kunz
7,328,828 B2 2/2008 Ortiz et al.
7,364,061 B2 4/2008 Swayze et al.
7,380,695 B2 6/2008 Doll et al.
7,380,696 B2 6/2008 Shelton, IV et al.
7,404,508 B2 7/2008 Smith et al.
7,407,078 B2 8/2008 Shelton, IV et al.
7,416,101 B2 8/2008 Shelton, IV et al.
7,419,080 B2 9/2008 Smith et al.
7,422,139 B2 9/2008 Shelton, IV et al.
7,431,189 B2 10/2008 Shelton, IV et al.
7,441,684 B2 10/2008 Shelton, IV et al.
7,448,525 B2 11/2008 Shelton, IV et al.
7,464,846 B2 12/2008 Shelton, IV et al.
7,464,847 B2 12/2008 Viola et al.
7,464,849 B2 12/2008 Shelton, IV et al.
7,481,347 B2 1/2009 Roy
7,481,824 B2 1/2009 Boudreaux et al.
7,487,899 B2 2/2009 Shelton, IV et al.
7,549,564 B2 6/2009 Boudreaux
7,565,993 B2 7/2009 Milliman et al.
7,568,603 B2 8/2009 Shelton, IV et al.
7,575,144 B2 8/2009 Ortiz et al.
7,588,175 B2 9/2009 Timm et al.
7,588,176 B2 9/2009 Timm et al.
7,637,409 B2 12/2009 Marczyk
7,641,093 B2 1/2010 Doll et al.
7,644,848 B2 1/2010 Swayze et al.
7,670,334 B2 3/2010 Hueil et al.
7,673,780 B2 3/2010 Shelton, IV et al.
7,699,835 B2 4/2010 Lee et al.

(56) References Cited

U.S. PATENT DOCUMENTS 7,721,931 B2 5/2010 Shelton, IV et al.
7,738,971 B2 6/2010 Swayze et al.
7,740,159 B2 6/2010 Shelton, IV et al.
7,743,960 B2 6/2010 Whitman et al.
7,758,613 B2 7/2010 Whitman
7,766,210 B2 8/2010 Shelton, IV et al.
7,770,773 B2 8/2010 Whitman et al.
7,770,775 B2 8/2010 Shelton, IV et al.
7,793,812 B2 9/2010 Moore et al.
7,799,039 B2 9/2010 Shelton, IV et al.
7,802,712 B2 9/2010 Milliman et al.
7,803,151 B2 9/2010 Whitman
7,822,458 B2 10/2010 Webster, III et al.
7,845,534 B2 12/2010 Viola et al.
7,845,537 B2 12/2010 Shelton, IV et al.
7,857,185 B2 12/2010 Swayze et al.
7,870,989 B2 1/2011 Viola et al.
7,900,805 B2 3/2011 Shelton, IV et al.
7,905,897 B2 3/2011 Whitman et al.
7,918,230 B2 4/2011 Whitman et al.
7,922,061 B2 4/2011 Shelton, IV et al.
7,922,719 B2 4/2011 Ralph et al.
7,947,034 B2 5/2011 Whitman
7,951,071 B2 5/2011 Whitman et al.
7,954,682 B2 6/2011 Giordano et al.
7,959,051 B2 6/2011 Smith et al.
7,963,433 B2 6/2011 Whitman et al.
7,967,178 B2 6/2011 Scirica et al.
7,967,179 B2 6/2011 Olson et al.
7,992,758 B2 8/2011 Whitman et al.
8,011,550 B2 9/2011 Aranyi et al.
8,016,178 B2 9/2011 Olson et al.
8,016,855 B2 9/2011 Whitman et al.
8,020,743 B2 9/2011 Shelton, IV
8,025,199 B2 9/2011 Whitman et al.
8,035,487 B2 10/2011 Malackowski
8,052,024 B2 11/2011 Viola et al.
8,114,118 B2 2/2012 Knodel et al.
8,127,975 B2 3/2012 Olson et al.
8,132,705 B2 3/2012 Viola et al.
8,152,516 B2 4/2012 Harvey et al.
8,157,150 B2 4/2012 Viola et al.
8,157,151 B2 4/2012 Ingmanson et al.
8,182,494 B1 5/2012 Yencho et al.
8,186,555 B2 5/2012 Shelton, IV et al.
8,186,587 B2 5/2012 Zmood et al.
8,220,367 B2 7/2012 Hsu
8,235,273 B2 8/2012 Olson et al.
8,241,322 B2 8/2012 Whitman et al.
8,272,554 B2 9/2012 Whitman et al.
8,292,150 B2 10/2012 Bryant
8,292,888 B2 10/2012 Whitman
8,342,379 B2 1/2013 Whitman et al.
8,348,130 B2 1/2013 Shah et al.
8,348,855 B2 1/2013 Hillely et al.
8,353,440 B2 1/2013 Whitman et al.
8,357,144 B2 1/2013 Whitman et al.
8,365,633 B2 2/2013 Simaan et al.
8,365,972 B2 2/2013 Aranyi et al.
8,371,492 B2 2/2013 Aranyi et al.
8,372,057 B2 2/2013 Cude et al.
8,391,957 B2 3/2013 Carlson et al.
8,403,926 B2 3/2013 Nobis et al.
8,418,904 B2 4/2013 Wenchell et al.
8,424,739 B2 4/2013 Racenet et al.
8,454,585 B2 6/2013 Whitman
8,505,802 B2 8/2013 Viola et al.
8,517,241 B2 8/2013 Nicholas et al.
8,523,043 B2 9/2013 Ullrich et al.
8,551,076 B2 10/2013 Duval et al.
8,561,871 B2 10/2013 Rajappa et al.
8,561,874 B2 10/2013 Scirica
8,602,287 B2 12/2013 Yates et al.
8,623,000 B2 1/2014 Humayun et al.
8,627,995 B2 1/2014 Smith et al.
8,632,463 B2 1/2014 Drinan et al.
8,636,766 B2 1/2014 Milliman et al.
8,647,258 B2 2/2014 Aranyi et al.
8,652,121 B2 2/2014 Quick et al.
8,657,174 B2 2/2014 Yates et al.
8,657,177 B2 2/2014 Scirica et al.
8,672,206 B2 3/2014 Aranyi et al.
8,696,552 B2 4/2014 Whitman
8,708,213 B2 4/2014 Shelton, IV et al.
8,715,306 B2 5/2014 Faller et al.
8,758,391 B2 6/2014 Swayze et al.
8,806,973 B2 8/2014 Ross et al.
8,808,311 B2 8/2014 Heinrich et al.
8,820,605 B2 9/2014 Shelton, IV
8,851,355 B2 10/2014 Aranyi et al.
8,858,571 B2 10/2014 Shelton, IV et al.
8,875,972 B2 11/2014 Weisenburgh, II et al.
8,888,762 B2 11/2014 Whitman
8,893,946 B2 11/2014 Boudreaux et al.
8,899,462 B2 12/2014 Kostrzewski et al.
8,905,289 B2 12/2014 Patel et al.
8,919,630 B2 12/2014 Milliman
8,931,680 B2 1/2015 Milliman
8,939,344 B2 1/2015 Olson et al.
8,950,646 B2 2/2015 Viola
8,960,519 B2 2/2015 Whitman et al.
8,961,396 B2 2/2015 Azarbarzin et al.
8,967,443 B2 3/2015 McCuen
8,968,276 B2 3/2015 Zemlok et al.
8,968,337 B2 3/2015 Whitfield et al.
8,992,422 B2 3/2015 Spivey et al.
9,016,545 B2 4/2015 Aranyi et al.
9,023,014 B2 5/2015 Chowaniec et al.
9,033,868 B2 5/2015 Whitman et al.
9,055,943 B2 6/2015 Zemlok et al.
9,064,653 B2 6/2015 Prest et al.
9,072,515 B2 7/2015 Hall et al.
9,113,847 B2 8/2015 Whitman et al.
9,113,875 B2 8/2015 Viola et al.
9,113,876 B2 8/2015 Zemlok et al.
9,113,899 B2 8/2015 Garrison et al.
9,216,013 B2 12/2015 Scirica et al.
9,282,961 B2 3/2016 Whitman et al.
9,282,963 B2 3/2016 Bryant
9,295,522 B2 3/2016 Kostrzewski
9,307,986 B2 4/2016 Hall et al.
2001/0031975 A1 10/2001 Whitman et al.
2002/0049454 A1 4/2002 Whitman et al.
2002/0165541 A1 11/2002 Whitman
2003/0038938 A1 2/2003 Jung et al.
2003/0165794 A1 9/2003 Matoba
2004/0111012 A1 6/2004 Whitman
2004/0133189 A1 7/2004 Sakurai
2004/0153124 A1 8/2004 Whitman
2004/0176751 A1 9/2004 Weitzner et al.
2004/0193146 A1 9/2004 Lee et al.
2005/0125027 A1 6/2005 Knodel et al.
2005/0131442 A1 6/2005 Yachia et al.
2006/0142656 A1 6/2006 Malackowski et al.
2006/0142740 A1 6/2006 Sherman et al.
2006/0142744 A1 6/2006 Boutoussov
2006/0259073 A1 11/2006 Miyamoto et al.
2006/0278680 A1 12/2006 Viola et al.
2006/0284730 A1 12/2006 Schmid et al.
2007/0023476 A1 2/2007 Whitman et al.
2007/0023477 A1 2/2007 Whitman et al.
2007/0029363 A1 2/2007 Popov
2007/0084897 A1 4/2007 Shelton et al.
2007/0102472 A1 5/2007 Shelton
2007/0152014 A1 7/2007 Gillum et al.
2007/0175947 A1 8/2007 Ortiz et al.
2007/0175949 A1 8/2007 Shelton et al.
2007/0175950 A1 8/2007 Shelton et al.
2007/0175951 A1 8/2007 Shelton et al.
2007/0175955 A1 8/2007 Shelton et al.
2007/0175961 A1 8/2007 Shelton et al.
2007/0270784 A1 11/2007 Smith et al.
2008/0029570 A1 2/2008 Shelton et al.
2008/0029573 A1 2/2008 Shelton et al.

(56) References Cited

U.S. PATENT DOCUMENTS

| | | | |
|---|---|---|---|
| 2008/0029574 | A1 | 2/2008 | Shelton et al. |
| 2008/0029575 | A1 | 2/2008 | Shelton et al. |
| 2008/0058801 | A1 | 3/2008 | Taylor et al. |
| 2008/0109012 | A1 | 5/2008 | Falco et al. |
| 2008/0110958 | A1 | 5/2008 | McKenna et al. |
| 2008/0147089 | A1 | 6/2008 | Loh et al. |
| 2008/0167736 | A1 | 7/2008 | Swayze et al. |
| 2008/0185419 | A1 | 8/2008 | Smith et al. |
| 2008/0188841 | A1 | 8/2008 | Tomasello et al. |
| 2008/0197167 | A1 | 8/2008 | Viola et al. |
| 2008/0208195 | A1 | 8/2008 | Shores et al. |
| 2008/0237296 | A1 | 10/2008 | Boudreaux et al. |
| 2008/0251561 | A1 | 10/2008 | Eades et al. |
| 2008/0255413 | A1 | 10/2008 | Zemlok et al. |
| 2008/0255607 | A1 | 10/2008 | Zemlok |
| 2008/0262654 | A1 | 10/2008 | Omori et al. |
| 2008/0308603 | A1 | 12/2008 | Shelton et al. |
| 2009/0012533 | A1 | 1/2009 | Barbagli et al. |
| 2009/0090763 | A1 | 4/2009 | Zemlok et al. |
| 2009/0099876 | A1 | 4/2009 | Whitman |
| 2009/0138006 | A1 | 5/2009 | Bales et al. |
| 2009/0171147 | A1 | 7/2009 | Lee et al. |
| 2009/0182193 | A1 | 7/2009 | Whitman et al. |
| 2009/0209990 | A1 | 8/2009 | Yates et al. |
| 2009/0254094 | A1 | 10/2009 | Knapp et al. |
| 2009/0299141 | A1 | 12/2009 | Downey et al. |
| 2010/0023022 | A1 | 1/2010 | Zeiner et al. |
| 2010/0069942 | A1 | 3/2010 | Shelton, IV |
| 2010/0193568 | A1 | 8/2010 | Scheib et al. |
| 2010/0211053 | A1 | 8/2010 | Ross et al. |
| 2010/0225073 | A1 | 9/2010 | Porter et al. |
| 2011/0071508 | A1 | 3/2011 | Duval et al. |
| 2011/0077673 | A1 | 3/2011 | Grubac et al. |
| 2011/0121049 | A1 | 5/2011 | Malinouskas et al. |
| 2011/0125138 | A1 | 5/2011 | Malinouskas et al. |
| 2011/0139851 | A1 | 6/2011 | McCuen |
| 2011/0155783 | A1 | 6/2011 | Rajappa et al. |
| 2011/0155786 | A1 | 6/2011 | Shelton, IV |
| 2011/0172648 | A1 | 7/2011 | Jeong |
| 2011/0174099 | A1 | 7/2011 | Ross et al. |
| 2011/0184245 | A1 | 7/2011 | Xia et al. |
| 2011/0204119 | A1 | 8/2011 | McCuen |
| 2011/0218522 | A1 | 9/2011 | Whitman |
| 2011/0276057 | A1 | 11/2011 | Conlon et al. |
| 2011/0290854 | A1 | 12/2011 | Timm et al. |
| 2011/0295242 | A1 | 12/2011 | Spivey et al. |
| 2011/0295269 | A1 | 12/2011 | Swensgard et al. |
| 2012/0000962 | A1 | 1/2012 | Racenet et al. |
| 2012/0074199 | A1 | 3/2012 | Olson et al. |
| 2012/0089131 | A1 | 4/2012 | Zemlok et al. |
| 2012/0104071 | A1 | 5/2012 | Bryant |
| 2012/0116368 | A1 | 5/2012 | Viola |
| 2012/0143002 | A1 | 6/2012 | Aranyi et al. |
| 2012/0172924 | A1 | 7/2012 | Allen, IV |
| 2012/0211542 | A1 | 8/2012 | Racenet |
| 2012/0223121 | A1 | 9/2012 | Viola et al. |
| 2012/0245428 | A1 | 9/2012 | Smith et al. |
| 2012/0253329 | A1 | 10/2012 | Zemlok et al. |
| 2012/0310220 | A1 | 12/2012 | Malkowski et al. |
| 2012/0323226 | A1 | 12/2012 | Chowaniec et al. |
| 2012/0330285 | A1 | 12/2012 | Hartoumbekis et al. |
| 2013/0018361 | A1 | 1/2013 | Bryant |
| 2013/0093149 | A1 | 4/2013 | Saur et al. |
| 2013/0181035 | A1 | 7/2013 | Milliman |
| 2013/0184704 | A1 | 7/2013 | Beardsley et al. |
| 2013/0214025 | A1 | 8/2013 | Zemlok et al. |
| 2013/0274722 | A1* | 10/2013 | Kostrzewski .... A61B 17/00234 606/1 |
| 2013/0282052 | A1 | 10/2013 | Aranyi et al. |
| 2013/0292451 | A1 | 11/2013 | Viola et al. |
| 2013/0313304 | A1 | 11/2013 | Shelton, IV et al. |
| 2013/0317486 | A1 | 11/2013 | Nicholas et al. |
| 2013/0319706 | A1 | 12/2013 | Nicholas et al. |
| 2013/0324978 | A1 | 12/2013 | Nicholas et al. |
| 2013/0324979 | A1 | 12/2013 | Nicholas et al. |
| 2013/0334281 | A1 | 12/2013 | Williams |
| 2014/0012236 | A1 | 1/2014 | Williams et al. |
| 2014/0012237 | A1 | 1/2014 | Pribanic et al. |
| 2014/0012289 | A1 | 1/2014 | Snow et al. |
| 2014/0025046 | A1 | 1/2014 | Williams et al. |
| 2014/0110455 | A1 | 4/2014 | Ingmanson et al. |
| 2014/0207125 | A1 | 7/2014 | Applegate et al. |
| 2014/0207182 | A1 | 7/2014 | Zergiebel et al. |
| 2014/0207185 | A1 | 7/2014 | Goble et al. |
| 2014/0236173 | A1 | 8/2014 | Scirica et al. |
| 2014/0236174 | A1 | 8/2014 | Williams et al. |
| 2014/0276932 | A1 | 9/2014 | Williams et al. |
| 2014/0299647 | A1 | 10/2014 | Scirica et al. |
| 2014/0303668 | A1 | 10/2014 | Nicholas et al. |
| 2014/0358129 | A1 | 12/2014 | Zergiebel et al. |
| 2014/0361068 | A1 | 12/2014 | Aranyi et al. |
| 2014/0365235 | A1 | 12/2014 | DeBoer et al. |
| 2014/0373652 | A1 | 12/2014 | Zergiebel et al. |
| 2015/0014392 | A1 | 1/2015 | Williams et al. |
| 2015/0048144 | A1 | 2/2015 | Whitman |
| 2015/0076205 | A1 | 3/2015 | Zergiebel |
| 2015/0080912 | A1 | 3/2015 | Sapre |
| 2015/0112381 | A1 | 4/2015 | Richard |
| 2015/0122870 | A1 | 5/2015 | Zemlok et al. |
| 2015/0133224 | A1 | 5/2015 | Whitman et al. |
| 2015/0133957 | A1 | 5/2015 | Kostrzewski |
| 2015/0150547 | A1 | 6/2015 | Ingmanson et al. |
| 2015/0150574 | A1 | 6/2015 | Richard et al. |
| 2015/0157320 | A1 | 6/2015 | Zergiebel et al. |
| 2015/0157321 | A1 | 6/2015 | Zergiebel et al. |
| 2015/0164502 | A1 | 6/2015 | Richard et al. |
| 2015/0201931 | A1 | 7/2015 | Zergiebel et al. |
| 2015/0272577 | A1 | 10/2015 | Zemlok et al. |
| 2015/0297199 | A1 | 10/2015 | Nicholas et al. |
| 2015/0303996 | A1 | 10/2015 | Calderoni |
| 2015/0320420 | A1 | 11/2015 | Penna et al. |
| 2015/0327850 | A1 | 11/2015 | Kostrzewski |
| 2015/0342601 | A1 | 12/2015 | Williams et al. |
| 2015/0342603 | A1 | 12/2015 | Zergiebel et al. |
| 2015/0374366 | A1 | 12/2015 | Zergiebel et al. |
| 2015/0374370 | A1 | 12/2015 | Zergiebel et al. |
| 2015/0374371 | A1 | 12/2015 | Richard et al. |
| 2015/0374372 | A1 | 12/2015 | Zergiebel et al. |
| 2015/0374449 | A1 | 12/2015 | Chowaniec et al. |
| 2015/0380187 | A1 | 12/2015 | Zergiebel et al. |
| 2016/0095585 | A1 | 4/2016 | Zergiebel et al. |
| 2016/0095596 | A1 | 4/2016 | Scirica et al. |
| 2016/0106406 | A1 | 4/2016 | Cabrera et al. |
| 2016/0113648 | A1 | 4/2016 | Zergiebel et al. |
| 2016/0113649 | A1 | 4/2016 | Zergiebel et al. |

FOREIGN PATENT DOCUMENTS

| | | | |
|---|---|---|---|
| CN | 102247182 | A | 11/2011 |
| DE | 102008053842 | A1 | 5/2010 |
| EP | 0705571 | A1 | 4/1996 |
| EP | 1769754 | A1 | 4/2007 |
| EP | 2055243 | A2 | 5/2009 |
| EP | 2316345 | A1 | 5/2011 |
| EP | 2333509 | A1 | 6/2011 |
| EP | 2668910 | A2 | 12/2013 |
| ES | 2333509 | A1 | 2/2010 |
| JP | 08-038488 | | 2/1996 |
| JP | 2005-125075 | A | 5/2005 |
| KR | 20120022521 | A | 3/2012 |
| WO | 2011/108840 | A2 | 9/2011 |
| WO | 2012/040984 | A1 | 4/2012 |

OTHER PUBLICATIONS

Japanese Office Action corresponding to International Application No. JP 2011-084092 dated Jan. 14, 2016.

Extended European Search Report corresponding to International Application No. EP 12 19 7970.2 dated Jan. 28, 2016.

Chinese Office Action corresponding to International Application No. CN 201210560638.1 dated Oct. 21, 2015.

European Office Action corresponding to International Application No. EP 14 15 9056.2 dated Oct. 26, 2015.

(56) References Cited

OTHER PUBLICATIONS

Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
European Search Report dated Feb. 22, 2017, issued in EP Application No. 16193636.
Extended European Search Report corresponding to counterpart International Application No. EP 14 18 4882.0 dated May 12, 2015.
Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 9783.3 dated Sep. 3, 2015.
Extended European Search Report corresponding to counterpart International Application No. EP 15 16 9962.6 dated Sep. 14, 2015.

* cited by examiner

ADAPTER ASSEMBLY FOR SURGICAL DEVICES

BACKGROUND

1. Technical Field

The present disclosure relates generally to powered surgical devices. More specifically, the present disclosure relates to adapter and extension assemblies for selectively connecting end effectors to actuation units of powered surgical devices.

2. Background of Related Art

Powered surgical devices for use in surgical procedures are known. To permit reuse of the handle assemblies of powered surgical devices and so that the handle assembly may be used with a variety of end effectors, adapter assemblies have been developed for selective attachment to the handle assemblies and to a variety of end effectors. Following use, the adapter may be disposed of along with the end effector. In some instances, the adapter assemblies may be sterilized for reuse.

SUMMARY

An assembly for operably connecting an end effector to a handle assembly is provided. The adapter assembly includes a coupling assembly and first, second, and third drive assemblies. The first drive assembly extends from the coupling assembly, defines a first longitudinal axis, and includes a first drive screw. The second drive assembly extends from the coupling assembly and is received about the first drive assembly. The second drive assembly defines a second longitudinal axis and includes a second drive screw in direct engagement with the first drive screw. The third drive assembly extends from the coupling assembly and is received about the first and second drive assemblies. The third drive assembly defines a third longitudinal axis and includes a third drive screw in direct engagement with the second drive screw.

In embodiments, the coupling assembly includes first, second, and third connector sleeves. The first connector sleeve may operably connect the first drive assembly to a first rotation transmitting member of a handle assembly, the second connector sleeve may operably connect the second drive assembly to a second rotation transmitting member of the handle assembly, and the third connector sleeve may operably connect the third drive assembly to a third rotation transmitting member of the handle assembly.

Each of the first, second, and third drive assemblies may include a proximal drive shaft, a distal drive shaft, and a drive screw. The first drive assembly may include a first drive screw having a threaded portion and a trocar member operably received about the threaded portion. Rotation of the first drive screw may cause longitudinal movement of the trocar member. The first, second, and third longitudinal axes may be co-axial.

The first drive assembly may further include a thrust plate. The first drive screw may engage the thrust plate during operation of the first drive assembly. Each of the first, second, and third drive assemblies may include a bearing assembly for rotatably supporting the respective first, second and third drive screws.

The adapter assembly may further include a connection assembly configured for operable connection to a handle assembly. Each of the first, second, and third drive assemblies may include a housing plate for supporting the respective first, second, and third drive screws. The first, second, and third longitudinal axes may be offset from a longitudinal axis of a handle assembly.

The adapter assembly may further include an outer sleeve. Each of the first, second, and third drive assemblies may extend through the outer sleeve. A distal end of the outer sleeve may be configured for operable connection to an end effector.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 2:
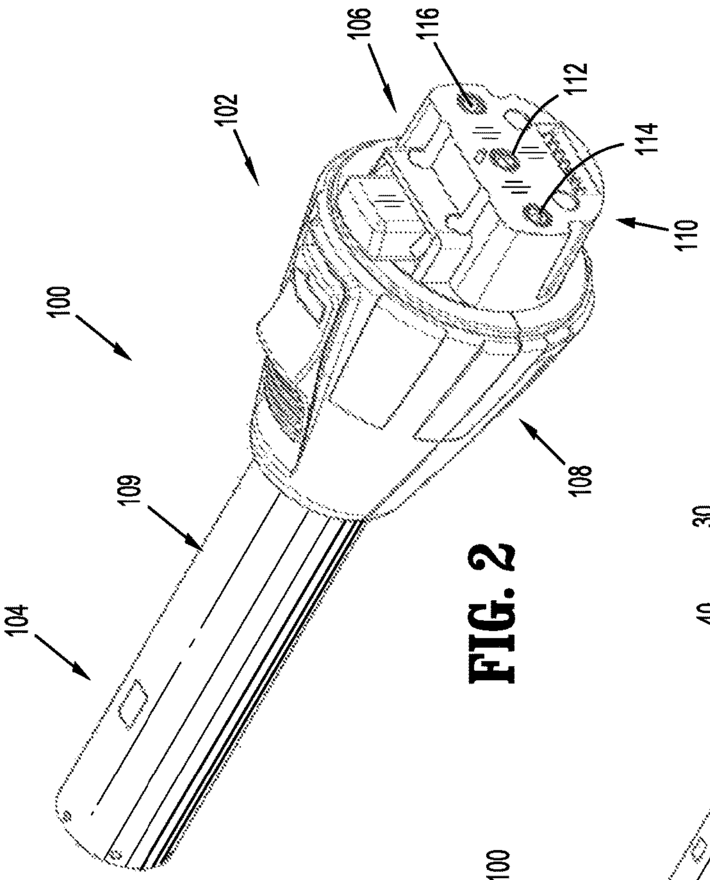
FIG. 2 is a perspective end view of the adapter assembly of FIG. 1.

Embodiments of the presently disclosed adapter assembly for surgical devices and/or handle assemblies are described in detail with reference to the drawings, in which like reference numerals designate identical or corresponding elements in each of the several views. As used herein the term “distal” refers to that portion of the adapter assembly or surgical device, or component thereof, farther from the user, while the term “proximal” refers to that portion of the adapter assembly or surgical device, or component thereof, closer to the user.

Figure 1:
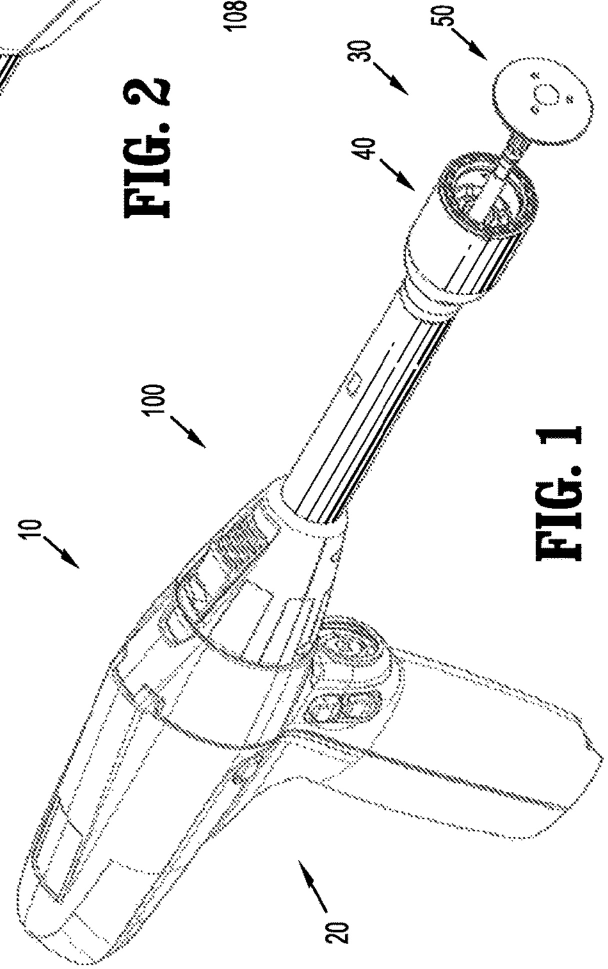
FIG. 1 is a perspective end view of an adapter assembly, in accordance with an embodiment of the present disclosure, secured to an exemplary handle assembly and with an exemplary tool assembly secured thereto.

With reference to FIG. 1, an adapter assembly in accordance with an embodiment of the present disclosure, shown generally as adapter assembly 100, is configured for selective connection to a powered hand-held electromechanical actuator shown, generally as handle assembly 20. As illustrated in FIG. 1, the adapter assembly 100 is configured for selective connection with the handle assembly 20. A tool assembly or end effector, e.g. tool assembly 30, which may, in exemplary embodiments, include a loading unit 40 and an anvil assembly 50, for applying a circular array of staples (not shown) to tissue (not shown) is configured for selective connection with the adapter assembly 100. The handle assembly 20, the adapter assembly 100, and the tool assembly 30 form a surgical stapling device 10. Although shown and described for use with a circular stapling loading unit, it is envisioned that the adapter assemblies of the present disclosure may be modified for use with stapling assembly having alternative configurations, and/or with non-stapling end effectors.

For a detailed description of the structure and function of an exemplary handle assembly, please refer to commonly owned U.S. Pat. Appl. Publ. No. 2012/0253329 ("the '329 application"), the content of which is incorporated by reference herein in its entirety.

Figure 3:
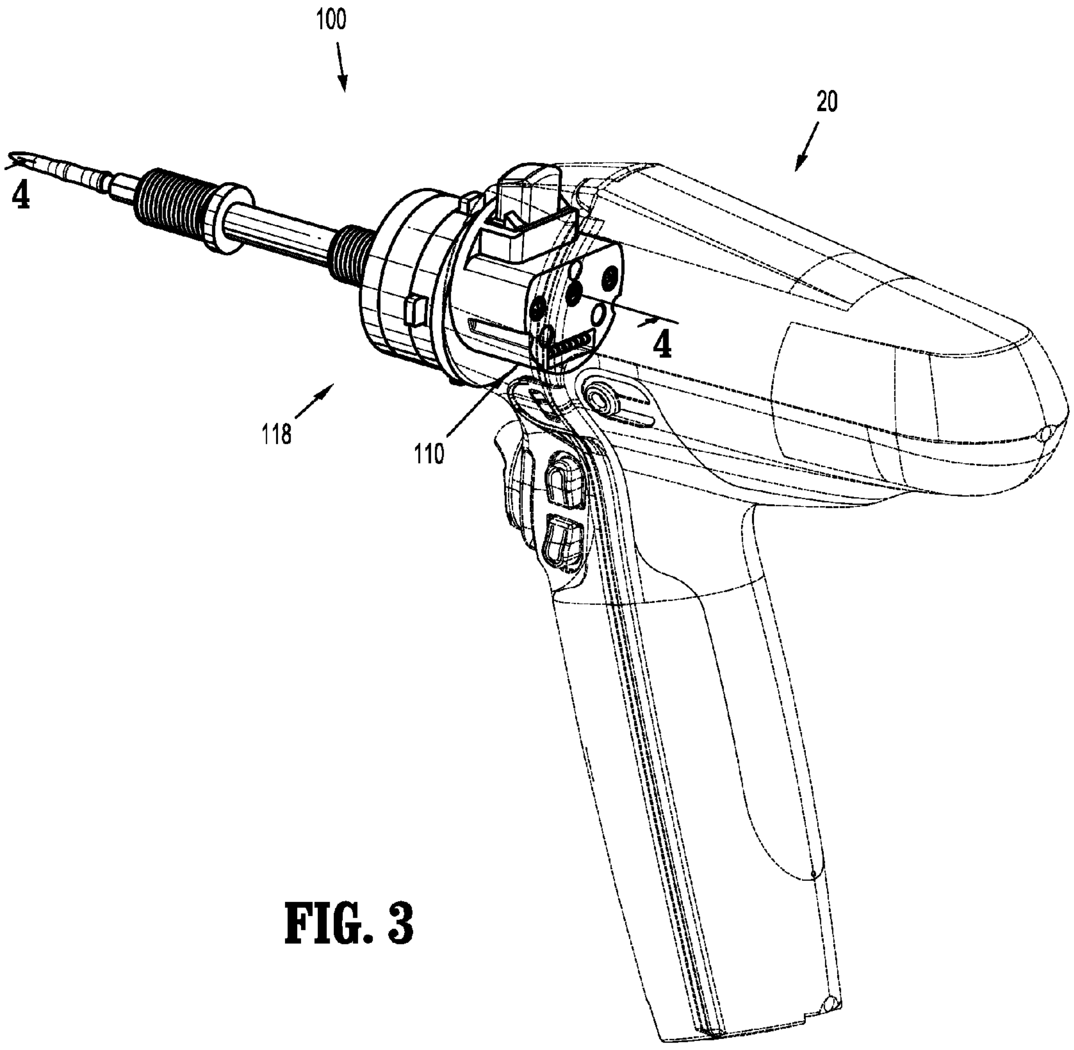
FIG. 3 is a perspective side view of the adapter assembly of FIG. 1 with a handle member and sleeve removed, and secured to the handle assembly of FIG. 1 (shown in phantom)

Referring initially to FIGS. 1-3, adapter assembly 100 includes a proximal portion 102 configured for operable connection to the handle assembly 20 (FIG. 1) and operable engagement by a user, and a distal portion 104 configured for operable connection to, and placement of, the tool assembly 30 (FIG. 1), including the loading unit 40 (FIG. 1) and the anvil assembly 50 (FIG. 1). More particularly, the proximal portion 102 of the adapter assembly 100 includes a base member 106, and a handle member 108 rotatably secured to the base member 106. The distal portion 104 includes a sleeve 109 fixedly secured to and extending from the handle member 108. A central longitudinal axis "x" (FIG. 4) of the adapter assembly 100 is offset a distance "d" (FIG. 4) from a central longitudinal axis "y" (FIG. 4) of the handle assembly 20 (FIG. 1). In one embodiment, the offset distance "d" is approximately 0.25 inches, while in another embodiment, the offset distance "d" is approximately 0.075 inches.

The adapter assembly 100 includes a coupling assembly 110 disposed within the base member 106 of the adapter assembly 100 for operatively connecting the drive shafts (not shown) of the handle assembly 20 with a drive mechanism 118 of the adapter assembly 100. The coupling assembly 110 includes first, second, and third connector sleeves 112, 114, 116 rotatably supported within the base member 106 of the adapter assembly 100. The first, second, and third connector sleeves 112, 114, 116 of the coupling assembly 110 operably connect respective, first, second, and third drive shafts (not shown) of the handle assembly 20 (FIG. 1) with respective first, second, and third drive assemblies 120, 140, 160 of the drive mechanism 118 of the adapter assembly 100. For a more detailed description of an exemplary coupling assembly, please refer to commonly owned U.S. Provisional Patent Application Ser. No. 62/066,518, filed Oct. 21, 2014, the content of which are incorporated herein by reference in its entirety.

Figure 6:
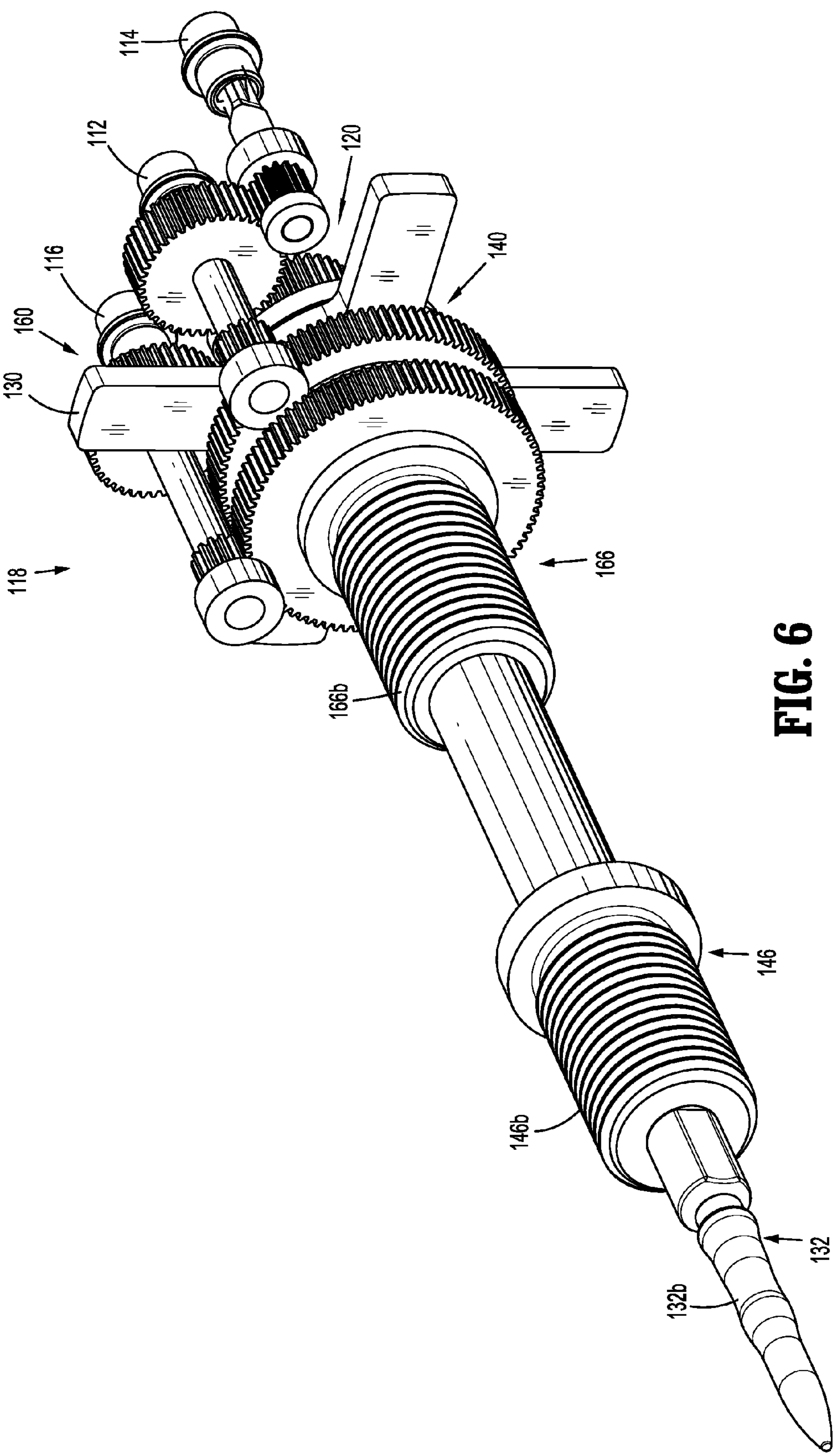
FIG. 6 is a perspective end view of a coupling assembly and a drive mechanism of the adapter assembly of FIG. 1.
Figure 7:
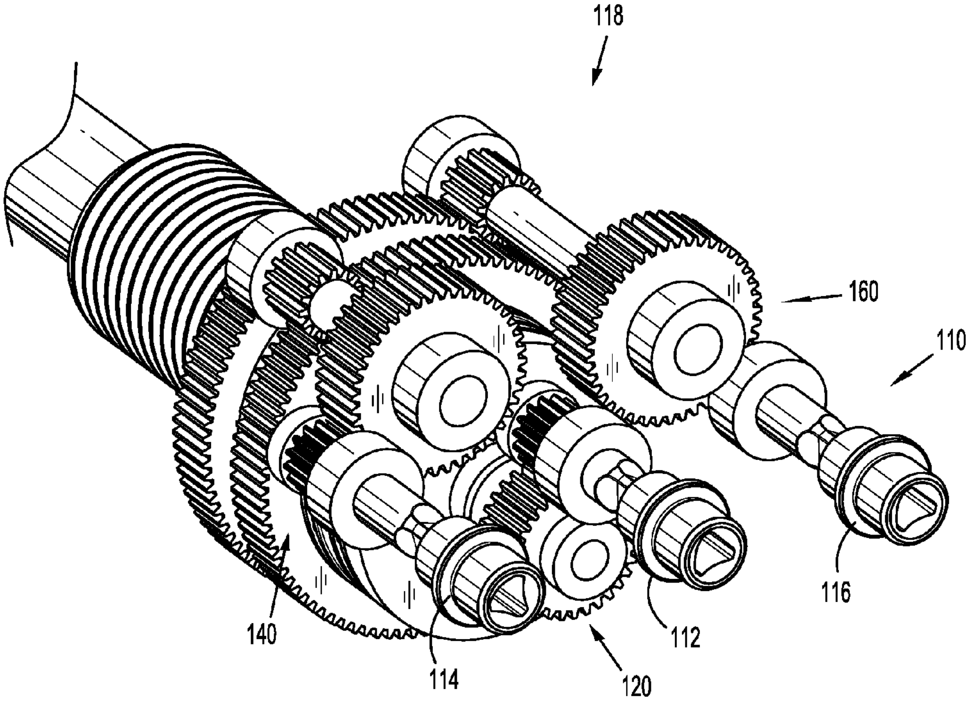
FIG. 7 is an enlarged perspective end view of the coupling assembly and the drive mechanism of FIG. 6.
Figure 8:
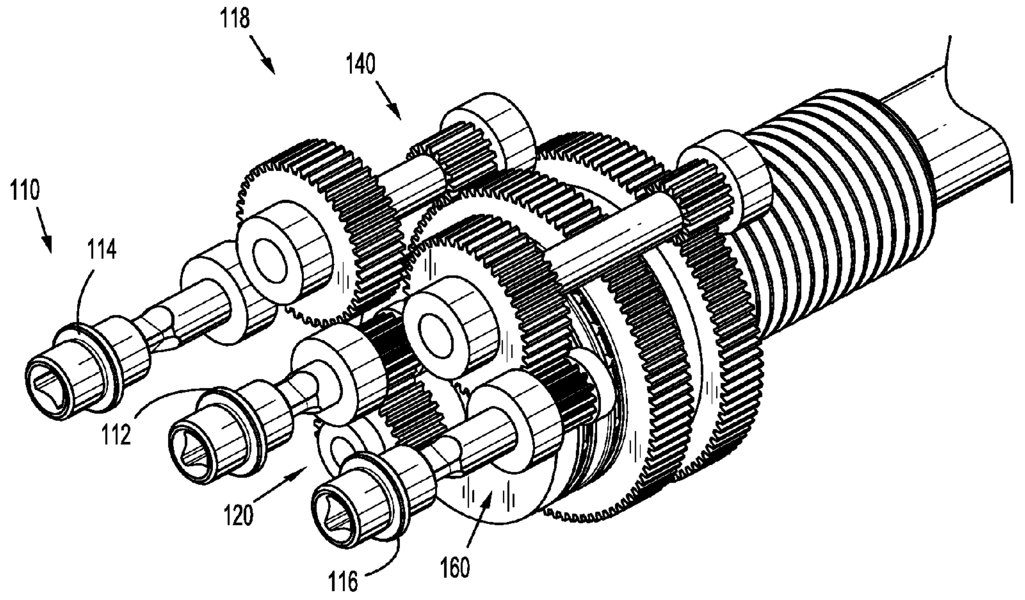
FIG. 8 is another enlarged perspective end view of the coupling assembly and the drive mechanism of FIG. 6.
Figure 10:
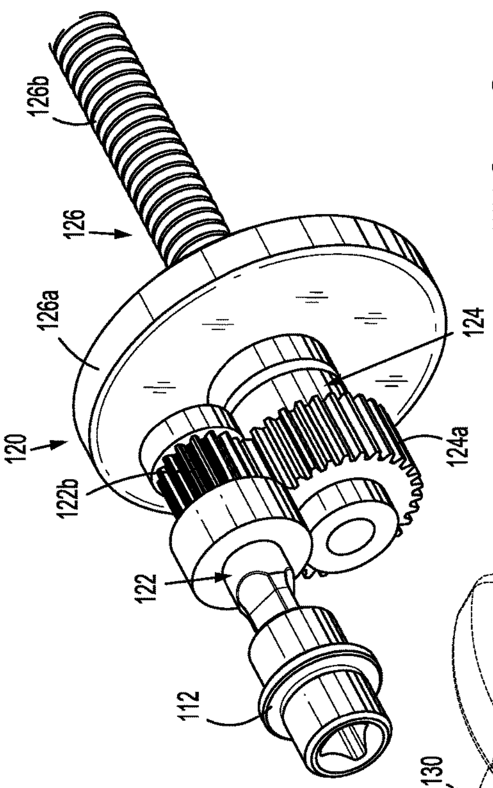
FIG. 10 is an enlarged perspective end view of a proximal end of the first drive assembly shown in FIG. 9.
Figure 9:
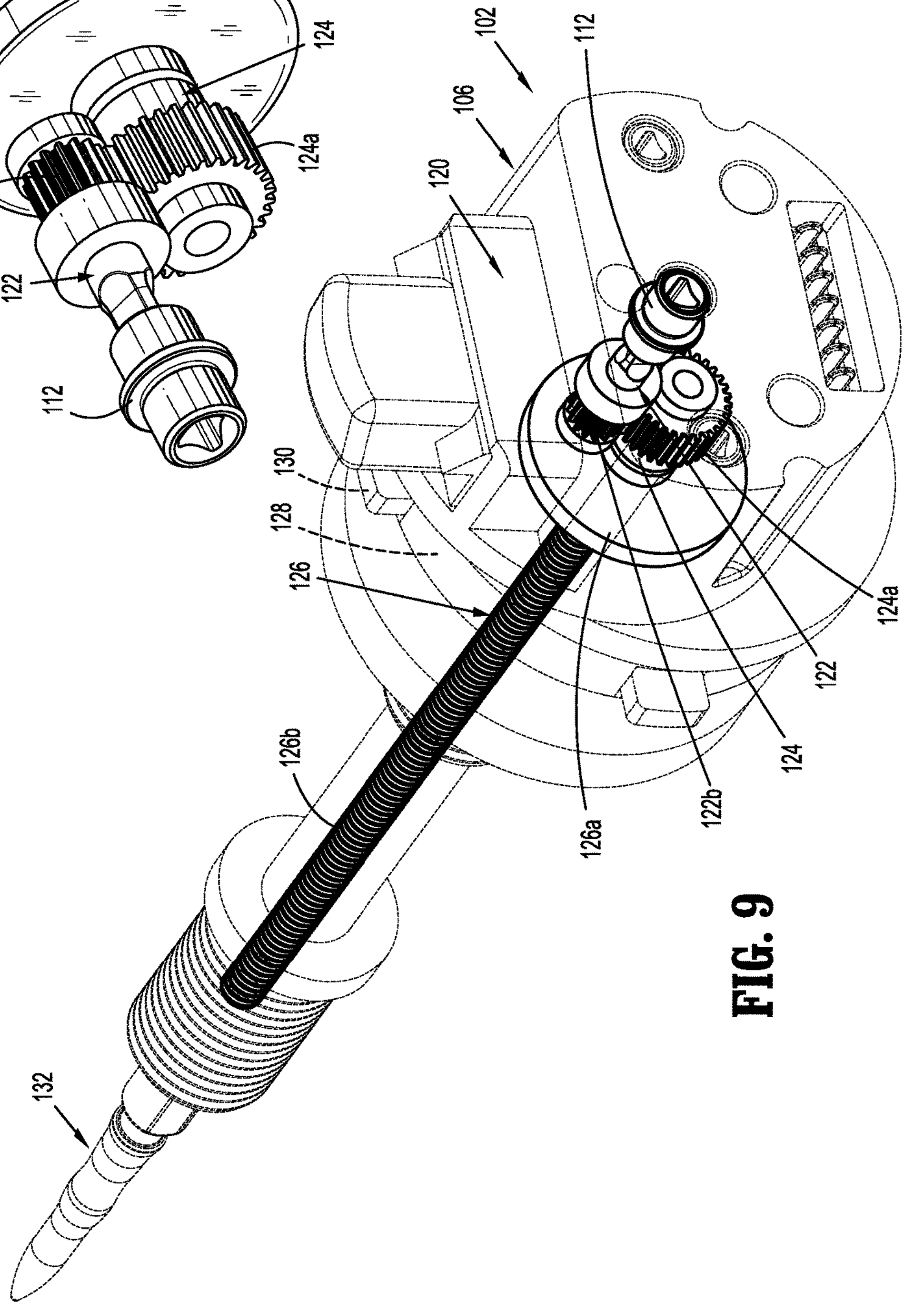
FIG. 9 is a perspective end view of a first drive assembly of the drive mechanism of FIG. 6 supported within a base member of the adapter assembly (shown in phantom)

With reference now to FIGS. 9 and 10, the first drive assembly 120 of the drive mechanism 118 (FIG. 6) of the adapter assembly 100 includes a first drive shaft 122 and a first distal drive shaft 124 rotatably supported within the base member 106, and a first drive screw 126 rotatably supported between a first housing plate 128 (FIG. 9; shown in phantom) and a thrust plate 130 (FIG. 9; shown in phantom). A proximal end of the first drive shaft 122 is operably connected to the first connector sleeve 112 of the coupling assembly 110. A distal end of the first drive shaft 122 includes a first drive gear **122*b* integrally formed therewith, or non-rotatably supported thereon. A proximal end of the first distal drive shaft 124 includes a second drive gear 124*a* integrally formed therewith, or non-rotatably supported thereon, operably connected with the first drive gear 122*b*. A distal end of the first distal drive shaft 124 is operably connected to the first drive screw 126. Although shown as separate components, it is envisioned that the first distal drive shaft 124 and the first drive screw 126 may be monolithically formed. A proximal end of the first drive screw 126 includes a gear flange 126*a* integrally formed therewith, or non-rotatably supported thereon. A distal end of the first drive screw 126 includes a threaded portion 126*b***.

Figure 5:
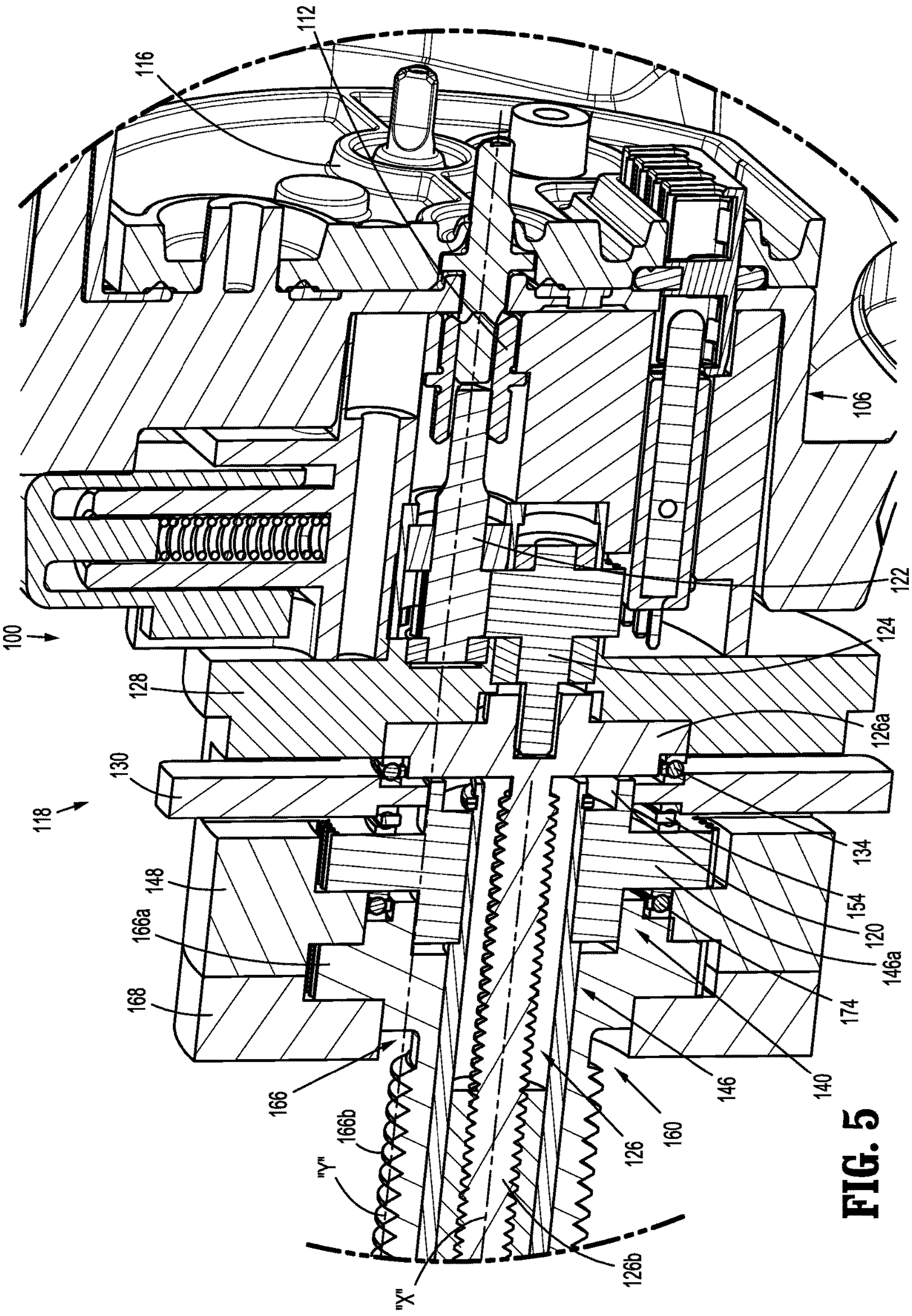
FIG. 5 is an enlarged view of the indicated area of detail of FIG. 4.

The gear flange **126*a* of the first drive screw 126 of the first drive assembly 120 is rotatably received between the first housing plate 128 (FIG. 9; shown in phantom) and the thrust plate 130 (FIG. 9; shown in phantom). A first bearing assembly 134 (FIG. 5) facilitates rotation of the first drive screw 126 between the first housing plate 128 and the thrust plate 130. Although not shown, the thrust plate 130 engages the handle member 108 of the adapter assembly 100 to distribute the load from the first drive assembly 120 to the handle member 108. A central longitudinal axis of the first drive screw 126 extends along the central longitudinal axis "x" of the adapter assembly 100**.

Figure 4:
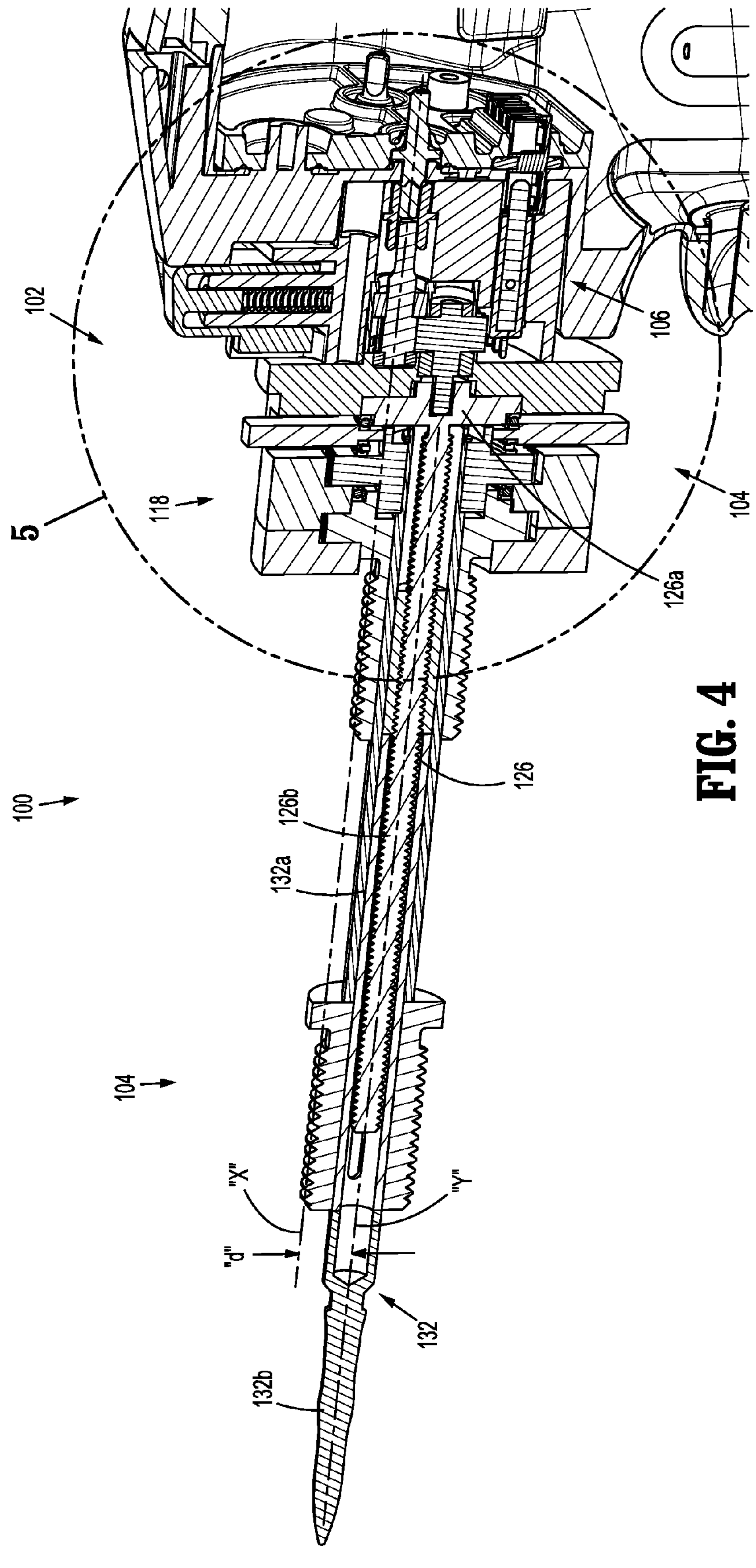
FIG. 4 is a cross-sectional side view taken along line 4-4 of FIG. 3.

As shown in FIG. 4, a threaded proximal end **132*a* of a trocar member 132 of the first drive assembly 120 is operably received about the threaded portion 126*b* of the first drive screw 126. Rotation of the first drive screw 126 about the longitudinal axis "x" effects longitudinal movement of the trocar member 132. When the anvil assembly 50 (FIG. 1) is secured to a distal end 132*b* of the trocar member 132, rotation of the first drive screw 126 in a first direction causes approximation of the anvil assembly 50 relative to the loading unit 40 (FIG. 1). Conversely, rotation of the first drive screw 126 in a second direction causes the anvil assembly 50 to move away from the loading unit 40. Alternatively, the first drive screw 126 operatively connects to a linearly or rotationally actuated assembly (not shown) of an end effector (not shown) for effecting performance of a first function, e.g., clamping tissue (not shown). In one embodiment, the thrust plate 130 may include a strain gauge for measuring the clamping forces during operation of the first drive assembly 120. By changing the size of the first and second drive gears 122*b*, 124*a* of the first drive assembly 120, the rate at which the drive screw 126 rotates relative to the input from the handle assembly 20** may be varied.

Figure 11:
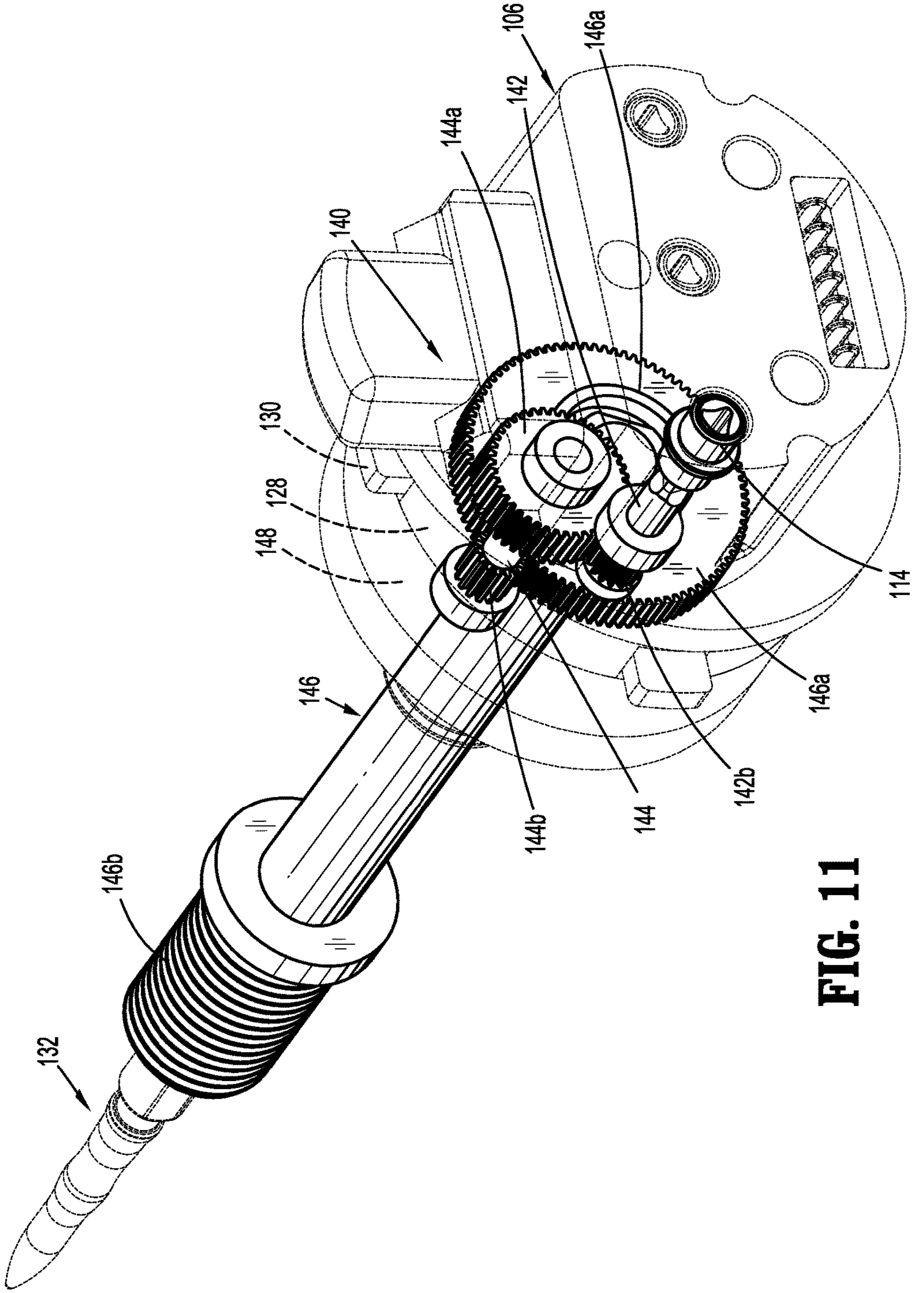
FIG. 11 is a perspective end view of a second drive assembly of the drive mechanism of FIG. 6 supported within the base member of the adapter assembly (shown in phantom)
Figure 12:
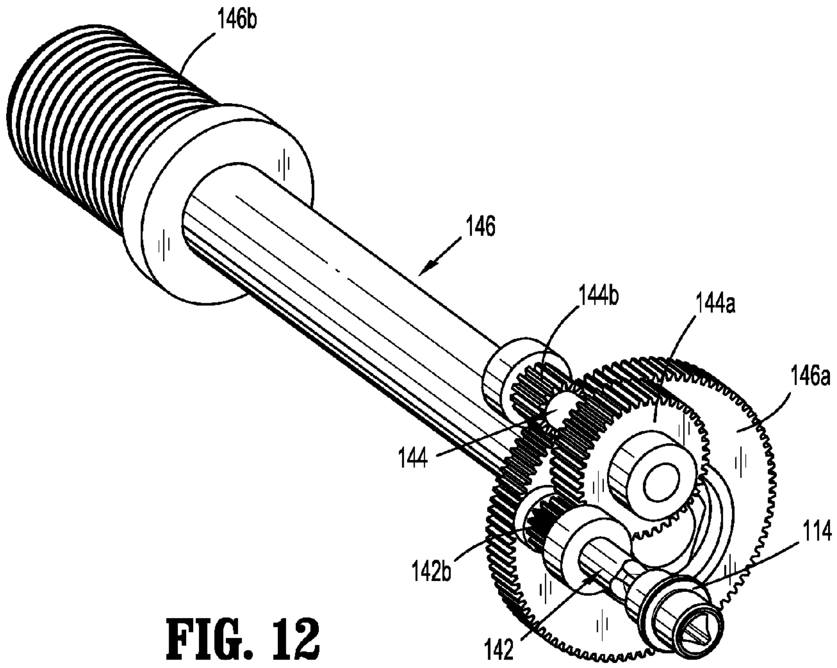
FIG. 12 is a perspective end view of the second drive assembly shown in FIG. 11.
Figure 13:
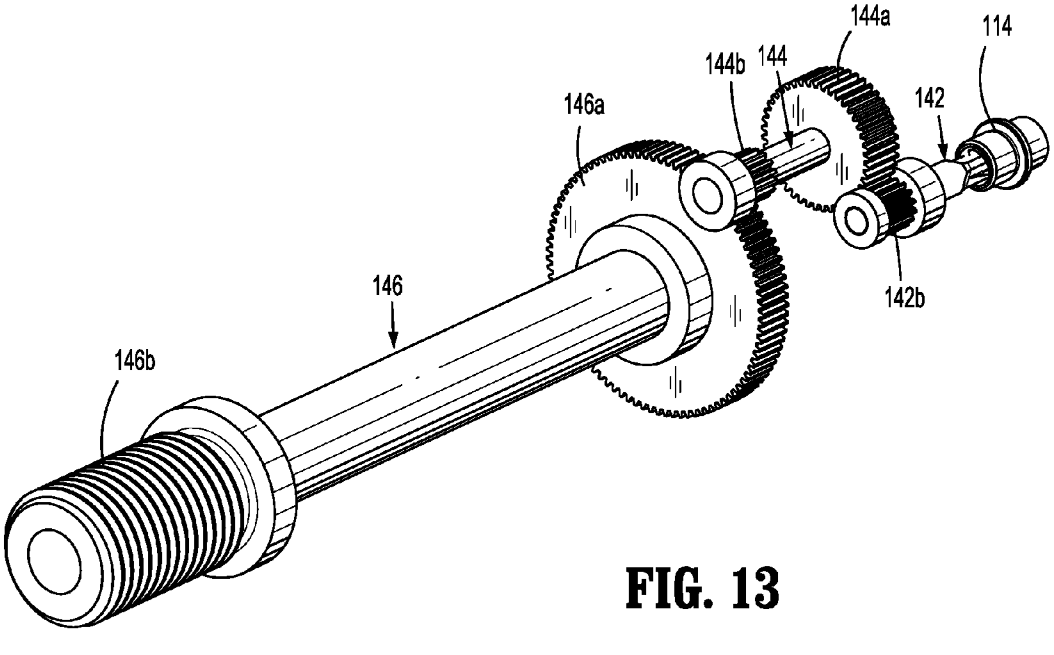
FIG. 13 is another perspective end view of the second drive assembly shown in FIG. 11.

With reference now to FIGS. 11-13, the second drive assembly 140 of the drive mechanism 118 (FIG. 6) of the adapter assembly 100 (FIG. 1) includes a second drive shaft 142 and a compound gear shaft 144 rotatably supported within the base member 106, and a second drive screw 146 rotatably supported between the gear flange **126*a* of the first drive screw 126 and a second housing plate 148. As will be described in further detail below, when the second drive screw 146 of the second drive assembly 140 experiences a load in the proximal direction, engagement of the second drive screw 146 with the first drive screw 126 of the first drive assembly 120 distributes the load from the second drive assembly 140 to the first drive assembly 120. This arrangement balances the load experienced in the first drive assembly 120, i.e., in the distal direction, with the load experienced in the second drive assembly 140, i.e., in the proximal direction, during operation of the adapter assembly 100**.

A proximal end of the second drive shaft 142 of the second drive assembly 140 is operably connected to the second connector sleeve 114 of the coupling assembly 110. A distal end of the second drive shaft 142 includes a first drive gear **142*b* integrally formed therewith, or non-rotatably supported thereon. A proximal end of the compound gear shaft 144 includes a second drive gear 144*a* integrally formed therewith, or non-rotatably supported thereon and a distal end of the compound gear shaft 144 includes a third drive gear 144*b*. The second drive gear 144*a* is operably connected with the first drive gear 142*b* and the third drive gear is operably connected to the second drive screw 146. As shown, the second drive gear 144*a* includes a larger diameter than the third drive gear 144*b*. In this manner, the compound gear shaft 146 operates to reduce the output speed and increase the output torque delivered to the second drive screw 146 from the handle assembly 20. In embodiments, the second compound gear shaft 146 replaces a planetary gear system (not shown), thereby saving space within the adapter assembly 100 and reducing the number of gears necessary for the operation of the adapter assembly 100**.

A proximal end of the second drive screw 146 includes a gear flange **146*a* integrally formed therewith, or non-rotatably supported thereon, in operable engagement with the third drive gear 144*b* of the compound gear shaft 144. A distal end of the second drive screw 146 includes a threaded portion 146*b*. The second drive screw 146 of the second drive assembly 140 is received about the threaded portion 126*b* of the first drive screw 126 of the first drive assembly 120 and accommodates receipt of the trocar member 132 of the first drive assembly 120 about the threaded portion 126*a* of the first drive screw 126**.

The gear flange **146*a* of the second drive screw 146 of the second drive assembly 140 is rotatably received between the gear flange 126*a* of the first drive screw 126 and the second housing plate 148. A second bearing assembly 154 facilitates rotation of the second drive screw 146 between the gear flange 126*a* of the first drive screw 126 and the second housing plate 148. A central longitudinal axis of the second drive screw 146 extends along the central longitudinal axis "x" (FIG. 4) of the adapter assembly 100**.

The threaded portion **146*b* of the second drive screw 146 operably connects to a linearly or rotationally actuated assembly (not shown) of the loading unit 40 (FIG. 1) of the tool assembly 30 (FIG. 1**), or other suitable end effector, for effecting performance of a second function, e.g., stapling tissue (not shown).

Figures 14, 15:
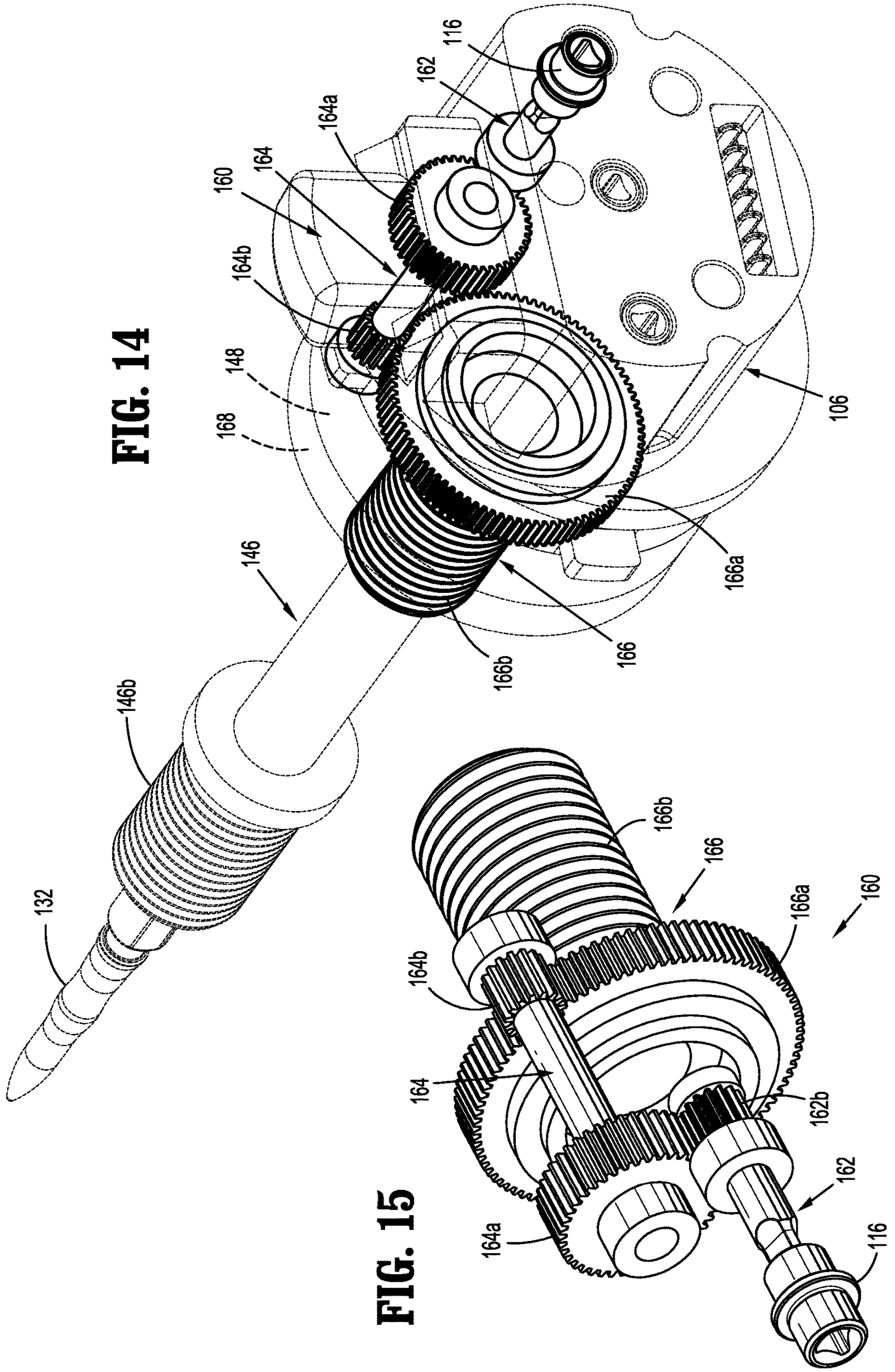
FIG. 14 is a perspective end view of a third drive assembly of the drive mechanism of FIG. 6 supported within the base member of the adapter assembly (shown in phantom)
FIG. 15 is a perspective end view of the third drive assembly shown in FIG. 14.

With reference now to FIGS. 15 and 16, the third drive assembly 160 of the drive mechanism 118 of the adapter assembly 100 includes a third drive shaft 162 and a compound gear shaft 164 rotatably supported within the base member 106, and a third drive screw 166 rotatably supported between the gear flange **146*a* of the second drive screw 146 and a third housing plate 168. As will be described in further detail below, when the third drive screw 166 of the third drive assembly 160 experiences a load in the proximal direction, engagement of the third drive screw 166 of the third drive assembly 160 with the second drive screw 146 of the second drive assembly 140, and engagement of the second drive screw 146 of the second drive assembly 140 with the first drive screw 126 of the first drive assembly 120, distributes the loads from the second and third drive assemblies 140, 160 to the first drive assembly 120. This arrangement balances the load experienced in the first drive assembly 120, i.e., in the distal direction, with the loads experienced in the second and third drive assemblies 140, 160, i.e., in the proximal direction, during operation of the adapter assembly 100**.

A proximal end of the third drive shaft 162 of the third drive assembly 160 operably engages the third connector sleeve 116 of the coupling assembly 110. A distal end of the third drive shaft 162 includes a first drive gear **162*b* integrally formed therewith, or non-rotatably supported thereon. A proximal end of the compound gear shaft 164 includes a second drive gear 164*a* integrally formed therewith, or non-rotatably supported thereon, and a distal end of the compound gear shaft 164 includes a third drive gear 164*b*. The second drive gear 164*a* is operably connected with the first drive gear 162*b* and the third drive gear is operably connected to the second drive screw 166. As shown, the second drive gear 164*a* includes a larger diameter than the third drive gear 164*b*. In this manner, the compound gear shaft 164 operates to reduce the output speed and increase the output torque delivered to the third drive screw 166 from the handle assembly 20. In embodiments, the third compound gear shaft 164 replaces a planetary gear system (not shown) used in previous embodiments, thereby saving space within the adapter assembly 100 and reducing the number of gears necessary for the operation of the adapter assembly 100**.

A proximal end of the third drive screw 166 includes a gear flange **166*a* integrally formed therewith, or non-rotatably supported thereon, in operable engagement with the third drive gear 164*b* of the compound gear shaft 164. A distal end of the third drive screw 166 includes a threaded portion 166*b*. The third drive screw 166 of the third drive assembly 160 is received about the second drive screw 146 of the second drive assembly 140 between the gear flange 146*a* of the second drive screw 146 and the threaded portion 146*b* of the second drive screw 146**.

The gear flange **166*a* of the third drive screw 166 of the third drive assembly 160 is rotatably received between the gear flange 146*a* of the second drive screw 146 of the second drive assembly 140 and the third housing plate 168. A third bearing assembly 174 facilitates rotation of the third drive screw 166 of the third drive assembly 160 between the second flange 146*a* of the second drive screw 146 of the second drive assembly 140 and the third housing plate 168. A central longitudinal axis of the third drive screw 166 extends along the central longitudinal axis "x" of the adapter assembly 100. Accordingly, each of the central longitudinal axes of the first, second, and third drive assemblies 120, 140, 160 of the drive mechanism 118 extend along the central longitudinal axis "x" (FIG. 4) of the adapter assembly 100, i.e., the first second, and third drive screws 126, 146, 166 of the respective first, second, and third drive assemblies 120, 140, 160 are coaxial. In this manner, an end effector attached to the distal portion 104 of the adapter assembly 100** may be rotated about the central longitudinal axis "x" to facilitate rotational positioning of the end effector.

The threaded portion **166*b* of the third drive screw 166 of the third drive assembly 160 operably connects to a linearly or rotationally actuated assembly (not shown) of the loading unit 40 (FIG. 1) of the tool assembly 30 (FIG. 1**), or other suitable end effector, for effecting performance of a third function, e.g., cutting tissue (not shown).

The operation of adapter assembly 100 will now be described with reference to the figures. The adapter assembly 100 is secured to the handle assembly 20 (FIG. 1) and loading unit 40 of the tool assembly 30 (FIG. 1) is secured to the adapter assembly 100 in a traditional manner. Subsequent to placement of the anvil assembly 50 (FIG. 1) of the tool assembly 30 (FIG. 1) through tissue to be stapled (not shown) and/or the placement of the tissue to be stapled around the anvil assembly 50, e.g., with a purse-string suture, the anvil assembly 50 is secured to the trocar member 132 of the adapter assembly 100.

The handle assembly 20 may then be actuated to cause individual or simultaneous rotation of any of the first, second, and third drive shafts (not shown) of the handle assembly 20 to effect actuation of the respective first, second, and third drive assemblies 120, 140, 160 of the drive mechanism 118 of the adapter assembly 100.

Referring briefly to FIGS. 9 and 10, during actuation of the handle assembly 20 (FIG. 1) to actuate the first drive assembly 120, rotation of the first drive shaft (not shown) of the handle assembly 20 rotates the first connector sleeve 112, which rotates the first drive shaft 122, which rotates the first distal drive shaft 124 to cause rotation of the first drive screw 126. Rotation of the first drive screw 126 in the first direction causes longitudinal movement of the trocar member 132 in the proximal direction, i.e., retraction, and rotation of the first drive screw 126 in the second direction causes longitudinal movement of the trocar member 132 in the distal direction, i.e., advancement.

As noted above, during actuation of the first drive assembly 120 of the drive mechanism 118, the gear flange **126*a* of the first drive screw 126 engages the thrust plate 130. The configuration of the adapter assembly 100 is such that the thrust plate 130 only experiences load during actuation of the first drive assembly 120. In this manner, the adapter assembly 100 will have better resolution during operation than an adapter assembly (not shown) in which the thrust plate 130 experiences additional loads from the second and third drive assemblies 140, 160. As noted above, the thrust plate 130 may include a strain gauge for measuring the clamping forces during operation of the first drive assembly 120**.

Turning to FIGS. 11-13, during actuation of handle assembly 20 (FIG. 1) to actuate the second drive assembly 140, rotation of the second drive shaft (not shown) of handle assembly 20 rotates the second connector sleeve 114, which rotates the second drive shaft 142, which rotates the compound gear shaft 144 to cause rotation of the second drive screw 146. Rotation of the second drive screw 146 in the first direction causes longitudinal movement of an attached first pusher member (not shown) in a distal direction, i.e., advancement, and rotation of the second drive screw 146 in the second direction causes longitudinal movement of the attached pusher member (not shown) in a proximal direction, i.e., retraction. As noted above, during actuation of the second drive assembly 140 of the drive mechanism 118, the gear flange **146*a* of the second drive screw 146 engages the gear flange 126*a* of the first drive screw 126**.

Turning to FIGS. 14 and 15, during actuation of handle assembly 20 (FIG. 1) to actuate the third drive assembly 160, rotation of the third drive shaft (not shown) of handle assembly 20 rotates the third connector sleeve 116, which rotates the third drive shaft 162, which rotates the compound gear shaft 164 to cause rotation of the third drive screw 166. Rotation of the third drive screw 166 in the first direction causes longitudinal movement of an attached second pusher member (not shown) in a distal direction, i.e., advancement, and rotation of the third drive screw 166 in the second direction causes longitudinal movement of the attached pusher member (not shown) in a proximal direction, i.e., retraction. As noted above, during actuation of the third drive assembly 160 of the drive mechanism 118, the gear flange **166*a* of the third drive screw 166 engages the gear flange 146*a* of the second drive screw 146 which engages the gear flange 126*a* of the first drive screw 126**.

The axial load path of the adapter assembly 100 extends through the first, second, and third drive screws 126, 146, 166 of the respective first, second, and third drive assemblies 120, 140, 160. In this manner, the sleeve 109 of the adapter assembly does not experience loads from the second and third drive assemblies 140, 160. As noted above, the common central longitudinal axis of the first, second, and third drive assemblies 120, 140, 160 allows the sleeve 109 of the adapter assembly 100 to be rotated along the longitudinal axis "x" of the adapter assembly 100.

Any of the components described herein may be fabricated from either metals, plastics, resins, composites or the like taking into consideration strength, durability, wearability, weight, resistance to corrosion, ease of manufacturing, cost of manufacturing, and the like.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An adapter assembly for operably connecting an end effector to a handle assembly, the adapter assembly comprising:
- a coupling assembly;
- a first drive assembly extending from the coupling assembly, the first drive assembly including a first drive screw, the first drive screw defining a first longitudinal axis;
- a second drive assembly extending from the coupling assembly and received about the first drive assembly, the second drive assembly including a second drive screw in engagement with the first drive screw, the second drive screw defining a second longitudinal axis; and
- a third drive assembly extending from the coupling assembly and received about the first and second drive assemblies, the third drive assembly including a third drive screw in engagement with the second drive screw, the third drive screw defining a third longitudinal axis, wherein at least two of the first, second, and third longitudinal axes are co-axial.

2. The adapter assembly of claim 1, wherein the coupling assembly includes first, second, and third connector sleeves.

3. The adapter assembly of claim 2, wherein the first connector sleeve operably connects the first drive assembly to a first rotation transmitting member of a handle assembly, the second connector sleeve operably connects the second drive assembly to a second rotation transmitting member of the handle assembly, and the third connector sleeve operably connects the third drive assembly to a third rotation transmitting member of the handle assembly.

4. The adapter assembly of claim 1, wherein each of the first, second, and third drive assemblies include a proximal drive shaft, a distal drive shaft, and a drive screw.

5. The adapter assembly of claim 1, wherein the first drive screw includes a threaded portion and a trocar member operably received about the threaded portion, wherein rotation of the first drive screw causes longitudinal movement of the trocar member.

6. The adapter assembly of claim 1, wherein the first, second, and third longitudinal axes are co-axial.

7. The adapter assembly of claim 1, wherein the first drive assembly further includes a thrust plate, the first drive screw engaging the thrust plate during operation of the first drive assembly.

8. The adapter assembly of claim 1, wherein the first, second, and third drive assemblies include respective first, second, and third bearing assemblies for rotatably supporting the respective first, second and third drive screws.

9. The adapter assembly of claim 1, further including a connection assembly configured for operable connection to a handle assembly.

10. The adapter assembly of claim 1, wherein each of the first, second, and third drive assemblies includes a housing plate for supporting the respective first, second, and third drive screws.

11. The adapter assembly of claim 1, wherein the first, second, and third longitudinal axes are offset from a longitudinal axis of a handle assembly.

12. The adapter assembly of claim 1, further including an outer sleeve, wherein each of the first, second, and third drive assemblies extends through the outer sleeve.

13. The adapter assembly of claim 12, wherein a distal end of the outer sleeve is configured for operable connection to an end effector.

14. An adapter assembly for operably connecting an end effector to a handle assembly, the adapter assembly comprising:

a coupling assembly;

a first drive assembly extending from the coupling assembly, the first drive assembly including a first drive screw;

a second drive assembly extending from the coupling assembly, the second drive assembly including a second drive screw disposed within the first drive screw, wherein the second drive screw is in operable engagement with the first drive screw; and a third drive assembly extending from the coupling assembly, the third drive assembly including a third drive screw disposed within the first and second drive screws, wherein the third drive screw is in operable engagement with the second drive screw.

15. The adapter assembly of claim 14, wherein each of the first, second, and third drive screws define a longitudinal axis, the longitudinal axes of the first, second, and third screws being co-axial.

16. The adapter assembly of claim 14, wherein the third drive assembly further includes a thrust plate, the third drive screw engaging the thrust plate during operation of the third drive assembly.

17. The adapter assembly of claim 14, wherein the first, second, and third drive assemblies include respective first, second, and third bearing assemblies for rotatably supporting the respective first, second and third drive screws.

* * * * *